(12) United States Patent
Smolyarov et al.

(10) Patent No.: US 7,887,506 B1
(45) Date of Patent: Feb. 15, 2011

(54) SAFETY MECHANISM TO PREVENT ACCIDENTAL PATIENT INJECTION AND METHODS OF SAME

(75) Inventors: Boris V. Smolyarov, Voronezh (RU); Victor T. Rogatchev, Voronezh (RU); Victor N. Katov, Voronezh (RU); Nathaniel Leon, Lutherville, MD (US)

(73) Assignee: Pulse Needlefree Systems, Inc., Lenexa, KS (US)

( * ) Notice: Subject to any disclaimer, the term of this patent is extended or adjusted under 35 U.S.C. 154(b) by 1980 days.

(21) Appl. No.: 09/717,559

(22) Filed: Nov. 21, 2000

(51) Int. Cl.
*A61M 5/30* (2006.01)
(52) U.S. Cl. .................................................. 604/68
(58) Field of Classification Search ............. 604/68–72, 604/140, 141, 143, 148, 232, 131
See application file for complete search history.

(56) References Cited

U.S. PATENT DOCUMENTS

| | | | |
|---|---|---|---|
| 2,547,099 A * | 4/1951 | Smoot | 604/70 |
| 2,821,891 A | 2/1958 | Gorey | |
| 3,057,349 A | 10/1962 | Ismach | |
| 3,292,622 A | 12/1966 | Banker | |
| 3,461,867 A | 8/1969 | Zimmet et al. | |
| 3,515,130 A | 6/1970 | Tsujino | |
| 3,518,990 A | 7/1970 | Banker | |
| 3,526,225 A | 9/1970 | Isobe | |
| 3,540,444 A | 11/1970 | Moreland | |
| 3,788,315 A | 1/1974 | Laurens | |
| 3,805,783 A | 4/1974 | Ismach | |
| 3,838,689 A * | 10/1974 | Cohen | 604/90 |
| 3,853,125 A | 12/1974 | Clark et al. | |
| 4,103,684 A | 8/1978 | Ismach | |
| 4,124,024 A | 11/1978 | Schwebel et al. | |
| 4,165,739 A | 8/1979 | Doherty et al. | |
| 4,266,541 A | 5/1981 | Landau | |
| 4,331,146 A * | 5/1982 | Brignola | 604/200 |
| 4,403,986 A | 9/1983 | Dettbarn et al. | |
| 4,592,742 A | 6/1986 | Landau | |
| 4,596,556 A | 6/1986 | Morrow et al. | |
| 4,722,728 A | 2/1988 | Dixon | |
| 4,850,967 A | 7/1989 | Cosmai | |
| 4,854,760 A * | 8/1989 | Pike et al. | 401/134 |
| 4,874,367 A | 10/1989 | Edwards | |
| 4,913,699 A | 4/1990 | Parsons | |
| 5,000,737 A | 3/1991 | Free et al. | |
| 5,009,637 A | 4/1991 | Newman et al. | |

(Continued)

FOREIGN PATENT DOCUMENTS

EP 0526772 A1 2/1993

(Continued)

OTHER PUBLICATIONS

Cool. Click: A Needle-Free Device for Growth Hormone Delivery, *The Medical Letter*, vol. 43, No. 1095, pp. 2-3 (Jan. 8, 2001).

(Continued)

*Primary Examiner*—Manuel A Mendez
(74) *Attorney, Agent, or Firm*—Stinson Morrison Hecker LLP (57) ABSTRACT

Disclosed is a medical injection assembly in which the assembly is adapted to reduce the risk of accidental injection of a patient and prevent cross contamination of patients or injectors.

33 Claims, 4 Drawing Sheets

U.S. PATENT DOCUMENTS

| | | | |
|---|---|---|---|
| 5,049,125 A | 9/1991 | Accaries et al. | |
| 5,062,830 A | 11/1991 | Dunlap | |
| 5,063,905 A | 11/1991 | Farrell | |
| 5,085,647 A | 2/1992 | Henderson et al. | |
| 5,152,751 A | 10/1992 | Kozlowski | |
| 5,171,304 A | 12/1992 | Ris et al. | |
| 5,190,523 A | 3/1993 | Lindmayer | |
| 5,222,948 A | 6/1993 | Austin et al. | |
| 5,256,142 A | 10/1993 | Colavecchio | |
| 5,279,608 A | 1/1994 | Cherif Cheikh | |
| 5,312,335 A | 5/1994 | McKinnon et al. | |
| 5,334,144 A | 8/1994 | Alchas et al. | |
| 5,354,286 A | 10/1994 | Mesa et al. | |
| 5,399,163 A | 3/1995 | Peterson et al. | |
| 5,411,492 A | 5/1995 | Sturman et al. | |
| 5,456,388 A | 10/1995 | Honstein et al. | |
| 5,501,666 A | 3/1996 | Spielberg | |
| 5,503,627 A | 4/1996 | McKinnon et al. | |
| 5,512,043 A | 4/1996 | Verkaart | |
| 5,520,639 A | 5/1996 | Peterson et al. | |
| 5,536,249 A | 7/1996 | Castellano et al. | |
| 5,569,189 A | 10/1996 | Parsons | |
| 5,569,209 A | 10/1996 | Roitman | |
| 5,573,767 A | 11/1996 | Dufour et al. | |
| 5,584,182 A | 12/1996 | Althaus et al. | |
| 5,593,390 A | 1/1997 | Castellano et al. | |
| 5,599,302 A | 2/1997 | Lilley et al. | |
| 5,618,268 A | 4/1997 | Raines et al. | |
| 5,620,434 A | 4/1997 | Brony | |
| 5,643,211 A | 7/1997 | Sadowski et al. | |
| 5,697,917 A | 12/1997 | Sadowski et al. | |
| 5,704,911 A | 1/1998 | Parsons | |
| 5,713,875 A | 2/1998 | Tanner, II | |
| 5,716,346 A | 2/1998 | Farris | |
| 5,722,953 A | 3/1998 | Schiff et al. | |
| 5,728,074 A | 3/1998 | Castellano et al. | |
| 5,730,723 A | 3/1998 | Castellano et al. | |
| 5,733,600 A | 3/1998 | McCabe | |
| 5,746,714 A | 5/1998 | Salo et al. | |
| 5,746,733 A | 5/1998 | Capaccio et al. | |
| 5,755,696 A | 5/1998 | Caizza | |
| 5,769,138 A | 6/1998 | Sadowski et al. | |
| 5,776,125 A | 7/1998 | Dudar et al. | |
| 5,780,100 A | 7/1998 | McCabe et al. | |
| 5,782,802 A | 7/1998 | Landau | |
| 5,785,688 A | 7/1998 | Joshi et al. | |
| 5,788,675 A | 8/1998 | Mayer | |
| 5,800,388 A | 9/1998 | Schiff et al. | |
| 5,803,078 A | 9/1998 | Brauner | |
| 5,807,374 A | 9/1998 | Caizza et al. | |
| 5,814,024 A | 9/1998 | Thomson et al. | |
| 5,817,082 A | 10/1998 | Niedospial, Jr. et al. | |
| 5,820,601 A | 10/1998 | Mayer | |
| 5,820,621 A | 10/1998 | Yale et al. | |
| 5,827,244 A | 10/1998 | Boettger | |
| 5,830,193 A | 11/1998 | Higashikawa | |
| 5,832,971 A | 11/1998 | Yale et al. | |
| 5,833,213 A | 11/1998 | Ryan | |
| 5,833,668 A | 11/1998 | Aguilar | |
| 5,833,674 A | 11/1998 | Turnbull et al. | |
| 5,836,911 A | 11/1998 | Marzynski et al. | |
| 5,836,923 A | 11/1998 | Mayer | |
| 5,839,715 A | 11/1998 | Leinsing | |
| 5,840,061 A | 11/1998 | Menne et al. | |
| 5,840,062 A | 11/1998 | Gumaste et al. | |
| 5,846,233 A | 12/1998 | Lilley et al. | |
| 5,851,198 A | 12/1998 | Castellano et al. | |
| 5,858,001 A | 1/1999 | Tsals et al. | |
| 5,860,957 A | 1/1999 | Jacobsen et al. | |
| 5,860,961 A | 1/1999 | Gettig | |
| 5,860,962 A | 1/1999 | Lewandowski et al. | |
| 5,865,795 A | 2/1999 | Schiff et al. | |
| 5,865,796 A | 2/1999 | McCabe | |
| 5,899,880 A | 5/1999 | Bellhouse et al. | |
| 5,922,685 A | 7/1999 | Rakhmilevich et al. | |
| 5,938,637 A | 8/1999 | Austin et al. | |
| 6,004,286 A | 12/1999 | Bellhouse et al. | |
| 6,010,478 A | 1/2000 | Bellhouse et al. | |
| 6,013,050 A | 1/2000 | Bellhouse et al. | |
| D422,697 S | 4/2000 | Bellhouse et al. | |
| 6,053,889 A | 4/2000 | Heinzen et al. | |
| D428,650 S | 7/2000 | Bellhouse et al. | |
| 6,083,197 A | 7/2000 | Umbaugh | |
| 6,102,896 A | 8/2000 | Roser | |
| 6,132,395 A * | 10/2000 | Landau et al. | 604/68 |
| 6,135,979 A | 10/2000 | Weston | |
| 6,264,629 B1 * | 7/2001 | Landau | 604/68 |

FOREIGN PATENT DOCUMENTS

| | | | |
|---|---|---|---|
| EP | 0776224 B1 | | 8/1995 |
| EP | 0888790 A1 | | 7/1997 |
| EP | 0834330 | | 4/1998 |
| EP | 0776224 B1 | | 12/1998 |
| EP | 0788386 B1 | | 1/1999 |
| EP | 0888790 A1 | | 1/1999 |
| EP | 0888791 A1 | | 1/1999 |
| EP | 0799064 B1 | | 8/1999 |
| EP | 0951917 A2 | | 10/1999 |
| EP | 0951917 A3 | | 10/1999 |
| FR | 2629348 | | 3/1988 |
| FR | 2641190 | | 1/1989 |
| FR | 2629348 | | 10/1989 |
| FR | 2641190 | | 7/1990 |
| RO | 0106078 | | 2/1993 |
| RO | 0108150 | | 2/1994 |
| RU | 2008932 | | 3/1994 |
| RU | 2108117 | | 4/1998 |
| SU | 257697 | | 11/1968 |
| SU | 0257697 | | 11/1969 |
| SU | 373005 | | 3/1971 |
| SU | 0373005 | | 3/1973 |
| SU | 476876 | | 10/1977 |
| SU | 0718111 | | 2/1980 |
| SU | 718111 | | 2/1980 |
| SU | 1279636 | | 12/1986 |
| SU | 2008932 C1 | | 1/1990 |
| SU | 2108117 | | 1/1991 |
| WO | 9734652 A1 | | 9/1997 |
| WO | 9748485 A1 | | 12/1997 |
| WO | 9810750 | | 3/1998 |
| WO | 9813087 | | 4/1998 |
| WO | 9813470 A1 | | 4/1998 |
| WO | 9813470 A1 | | 4/1998 |
| WO | 9821364 | | 4/1998 |
| WO | 99/03529 | | 1/1999 |
| WO | 9901168 A1 | | 1/1999 |
| WO | 9901169 A1 | | 1/1999 |
| WO | 9908689 A1 | | 2/1999 |
| WO | 9927961 A1 | | 6/1999 |
| WO | 9903529 A2 | | 9/1999 |
| WO | 0013573 A1 | | 3/2000 |
| WO | 0014547 A1 | | 3/2000 |
| WO | 0019982 A1 | | 4/2000 |
| WO | 0023592 A2 | | 4/2000 |
| WO | 0023592 A3 | | 4/2000 |
| WO | 0026385 A1 | | 5/2000 |
| WO | WO 2004/069313 A1 | | 8/2004 |
| WO | WO 2006/073394 A1 | | 7/2006 |

OTHER PUBLICATIONS

Figge, et al., Anatomic Evaluation of a Jet Injection Instrument Designed to Minimize Pain and Inconvenience of Parental Therapy, *The American Practitioner*, vol. 3, No. 4, pp. 197-206 (Dec. 1948).

Brochure on Agro-Jet: Needle-Less Jet Injector by M.I.T.

Description and Operating Instructions for Hydraulic Needleless Injector by V/O Medexport in Moscow.

Dimache, et al., A Clinical, Epidemiological and Laboratory Study on Avoiding the Risk of Transmitting Viral Hepatitis During Vaccinations with the Dermojet Protected by an Anticontaminant Disposable Device, *Vaccine*, vol. 15, No. 8, pp. 1010-1013 (1997).

Jet Gun Injection Transmission: A Clinical, Epidemiological and Laboratory Study on Avoiding the Risk of Transmitting Viral Hepatitis During Vaccinations with the Dermojet Protected by an Anticontaminant Disposable Device, *American Journal of Infection Control*, vol. 26, No. 4, pp. 442-445 (Aug. 1998).

Figge, et al., *Anatomic Evaluation of a Jet Injection Instrument Designed to Minimize Pain and Inconvenience of Parenteral Therapy*, AMER. PRAC., Dec. 1948, vol. III, No. 4., pp. 197-206.

*Cool. Click: A Needle-Free Device for Growth Hormone Delivery*, The Medical Letter, vol. 43 (Issue 1095), Jan. 8, 2001.

Examination Report dated Aug. 7, 2007 from the Canadian Intellectual Property Office in Canadian Patent Application No. 2,392,599.

Examination Report dated Jul. 30, 2007 from the Canadian Intellectual Property Office in Canadian Patent Application No. 2,392,598.

Examination Report dated Jul. 27, 2007 from the Canadian Intellectual Property Office in Canadian Patent Application No. 2,387,326.

* cited by examiner

SAFETY MECHANISM TO PREVENT ACCIDENTAL PATIENT INJECTION AND METHODS OF SAME

CROSS REFERENCE OF RELATED APPLICATIONS

This application claims priority to, and benefit from, U.S. patent application Ser. Nos. 09/685,499, filed 10 Oct. 2000; 09/685,633, filed 10 Oct. 2000; and Russian Patent Application No. 99124268, filed 23 Nov. 1999, which is now Russian Patent No. 2152228; the disclosures of which are entirely incorporated by reference herein to the extent permissible by law.

TECHNICAL FIELD OF THE INVENTION

The invention relates to a medical injection assembly in which the assembly is adapted to reduce the risk of accidental injection of a patient.

BACKGROUND OF THE INVENTION

The most effective measure to prevent many diseases is the mass immunization with vaccines. Since medical science has come to understand the principles of viral theory and its importance to the transmission of diseases, the need to break the viral or bacterial transmission chain from host to host has become well-established. There are wide varieties of methodologies accepted by medical science to break the chain depending on the requirements of the situation. The most stringent protocols include: sterilization, disinfection, and sanitization utilizing heat chemicals and/or ionizing radiation.

Barriers are another common protocol and can be as simple as establishing an imaginary boundary where one side of the boundary is kept clean and the other is defined as contaminated. Any object being transferred from the clean to the contaminated side of the boundary is not returned to the clean side without being disinfected, sanitized, or sterilized. A typical example of this type of protocol is within the medical surgical fields. The surface of the operating table is defined as the boundary. Any item that is dropped below the surface of the operating table is immediately defined as contaminated. This includes surgical implements or the surgeon's hands.

With needle injection devices there are two common protocols both of which start from the premise that a used syringe is, by definition, contaminated. The first, which is commonly used in dentistry, uses syringes and sometimes needles that are sterilized after each use. The second is more commonly used in general medicine in the U.S. and other developed countries. This is the disposable syringe and needle assembly. Because of the low cost of production typically—less than $0.10 per syringe assembly—this protocol is well-accepted.

Jet injector systems on the other hand continue to be characterized by relatively high cost per injection ($1.00 or more) when the syringe portion of the injector is discarded with each use. Additionally, there is the challenge in developing countries where lack of understanding of viral theory and/or a general hoarding mentality discourages following generally accepted protocols within all aspects of health and hygiene. With the identification of blood-borne pathogens like HIV, Hepatitis B, Hepatitis C and others, the need to follow proper protocols becomes more critical.

In the past, jet injectors such as Ped-O-Jet®, Ammo-Jet®, and similar mass campaign jet injectors were brought to health care systems. Such injectors had no provision for preventing the transfer of blood-borne pathogens except through the complicated disassembly and disinfecting process. In mass immunization campaigns these types of injector systems fell out of favor starting in the mid and late 1980's when it was determined that bodily fluids are easily transmitted from one patient to another.

To eliminate the possible transmission of blood-borne pathogens between individuals, disposable or partially disposable jet injector systems were developed. Bio-Jet®, J-Tip®, and others characterize this type of jet injector. General acceptance of these units is limited by relatively high direct costs, even in developed countries like the United States. The standard paradigm of breaking the contamination transmission chain has been addressed by either syringe disposal or designing the syringe so it can easily be decontaminated. Currently, there exists a steadily growing danger of the epidemic diseases (AIDS, hepatitis, tuberculosis and other viral diseases transferred through blood) being transmitted between individuals through the use of needleless injectors.

The traditional needleless injectors comprise the basic design, a housing with an inner power unit, a medication unit, and a nozzle. The function of the power unit pumps the medication into an under-plunger cavity of the medication unit chamber and to expel the medication through the nozzle.

At the initial stage of needleless injector development, when no check valves were used as a control for the functioning of the medication chamber, a method to prevent foreign particles from entering the injector nozzle was to use a sealed nozzle cap. Such cap was limited by the filling of the medication chamber with medication and could not guarantee contamination prevention.

Another approach to the contamination prevention problem has been the use of a disposable, low cost, one-shot nozzle assembly for jet injectors. The nozzle assembly comprises a two-piece molded device incorporating a generally cylindrical nozzle body having a central longitudinal bore of a predefined diameter, extending from a proximal end of the nozzle towards its distal end, terminating in a conical portion of the nozzle. A very small diameter jet-forming bore is formed at the apex of the conical portion of the bore in general. The disadvantage of this device is its lower efficiency (i.e., low vaccination rate) because of poor flow due to the conical design. Moreover, a plastic nozzle element also increases the vaccination cost.

A typical jet injector design has additional drawbacks. Even in the practice of using a protective cap, there is a possibility of infection transfer from one person to another by means of fluids (blood, lymph, medication) reflected from the skin surface during injection ("back splash") that may get on the nozzle and be transferred from one patient to the next. The protective cap can be a one-shot cap, including the injection nozzle. A purpose of this device is to prevent the multiple use of a cap with a nozzle. This is achieved through the removal, replacement, and/or destruction of the cap at the later stage of the injection. However, cross-contamination continues to be problematic because in the injection stage, the contaminated matter can be transferred through the nozzle to inside the injector such as, for example, into the cavity and be transmitted to a new patient through a new cap and nozzle.

With all the known devices, there is no guarantee that the minimum safety requirements for cross-contamination prevention, as recently introduced (Glenn Austin et al., *Gross Contamination Testing of Vaccine Jet Injectors, A Preliminary Report*, PATH, Seattle, Wash., 98109), will be achieved. Other studies indicate a very dangerous situation. For example, Russian and Brazilian studies have shown unfavorable data in up to 1.0% of the subjects studied—a level of risk far too great to ignore.

When jet injectors were introduced in the 1940's, they were popular for needle phobic patients or small veined patients. Improvements permitted jet injectors to administer hundreds of millions of vaccinations that saved countless lives. However, when the discovery of pathogen transfer occurred, jet injectors fell out of favor to such an extent that the WHO and the U.S. Department of Defense no longer recommended jet injector.

For example, in the mid-1980's an outbreak of Hepatitis B was caused by use of one high workload injector in a weight loss clinic. See, Canter et al., An Outbreak of Hepatitis B Associated With Jet Injections In A Weight Loss Clinic, Arch. Intern. Med., 150:1923-1927 (1990).

Present parenteral injection technology has recently been deemed by the World Health Organization (WHO) to be incompatible with their requirements for the planned Global Programme of Vaccination and Immunization (GPV) initiatives. It is estimated that 6 additional parenteral vaccines will be recommended for childhood vaccination by the year 2005, requiring a total of 3.6 billion immunization injections per year. The total number of parenteral injections, including injected drugs as well as vaccines, will be roughly ten times this number. This is in addition to the hundreds of millions needed in military induction centers, epidemic situations, worldwide immunizations, and veterinary uses. Major health care providers such as UNICEF, the WHO and CDC have recently confirmed that a radical new technology is required that can be used by personnel with minimal training and that is safer, more convenient, and more comfortable than the syringe and needle. (Jodar L., Aguado T., Lloyd J. and Lambert P-H, (1998) Revolutionizing Immunizations Gen. Eng. News 18, p. 6.)

In other words, what used to be a continent wide life saver, became an undesirable product. The present invention solves problems associated with pathogen transfer and solves many problems associated with the high costs of disposable units.

Coupled with this was that accidental discharge of the medication sometimes occurred. Premature injection could result in an incomplete injection or an injection in the improper situs.

Accordingly, there is a need in the art of needleless injection devices to solve the problem of cross-contamination during mass vaccinations. More particularly, there is a need for a protector designed for the nozzle head of needleless injectors, which halts "back splash" contamination, and which is low enough in cost to ensure its practical application as a disposable unit even for mass vaccinations. There is also a need to ensure that the incidence of premature discharge is reduced or eliminated.

SUMMARY OF THE INVENTION

The foregoing problems are solved and a technical advance is achieved by the present invention. Disclosed is medical injection assembly in which the assembly is adapted to reduce the risk of accidental injection of a patient. Manners of doing so include permitting the injection assembly to fire but blocking the medication stream or stopping the injection assembly from firing in the first place.

DETAILED DESCRIPTION OF THE INVENTION

Figure 1:
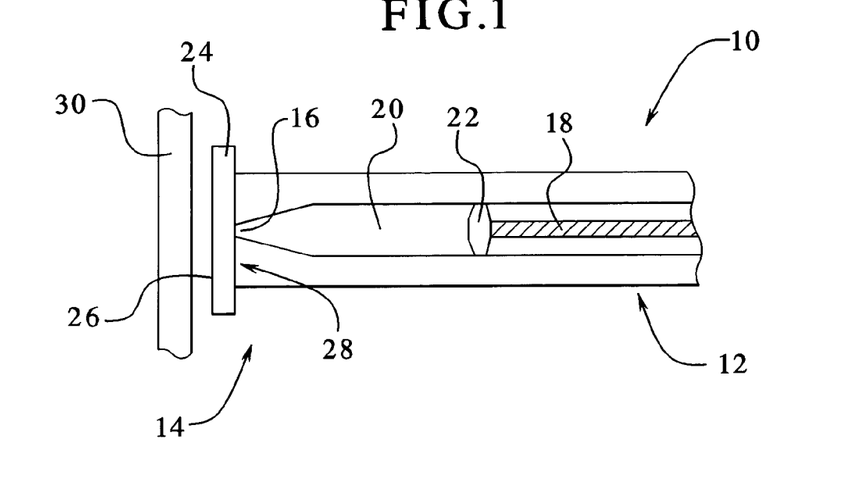
FIG. 1 is one simple embodiment of the invention showing the injector and cap.

FIG. 1 shows an embodiment of the invention. Disclosed is a medical device injection assembly 10. The injection assembly 10 further includes an injector assembly proximal end 12, an injector assembly distal end 14, and a distal end orifice 16. For the purposes of discussion, the terms distal and proximal are used to denote non-exclusive locations. The term "proximal" is used generally to describe the area normally closest to the physician or user. The term "distal" is used generally to describe the area close to the patient or close to the end where the medication exits the device. The medication is dispensed via an injection piston 18 located generally within the injector lumen 20. Medication is pushed out by the injector piston 18 and the injector head 22. As the medication flows, it passes through the cap 24, by passing through the cap proximal face 28 and through the cap distal face 26. The cap distal face 26 is the face that generally faces the patient's skin 30.

Figure 2:
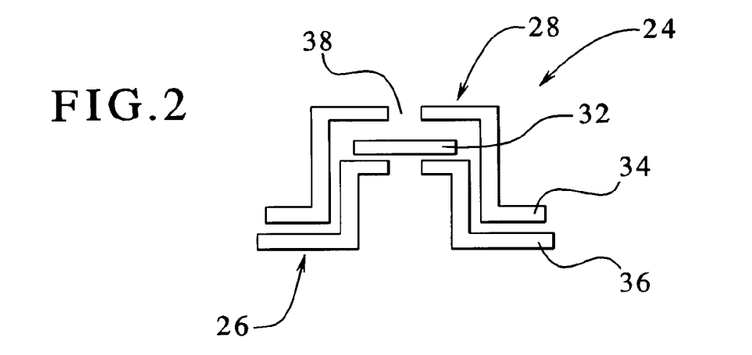
FIG. 2 is another embodiment of the invention showing one cap embodiment.

FIG. 2 demonstrates the cap. Although one configuration of the cap is shown, it should be understood that the cap may be configured in the many ways shown in U.S. patent application Ser. No. 09/685,499, the disclosure of which is expressly incorporated by reference herein. The cap 24 includes a cap distal face 26 and a cap proximal face 28. The cap 24 also includes a protective layer such as a film 32. The film 32 may comprise comprises at least one of a plastic, rubber, polymer, polyethylene, polytetrafloroethylene, polyurethane, polyolefin, polypropylene, and polysulfone material; or combination thereof. While the film 32 is shown sandwiched between a first component 34 and a second component 36, it is understood that the film 32 may be in other locations. The film 32 generally covers the cap orifice 38. Therefore, the various placements, configurations, or numbers of films present that permit the covering of the cap orifice 38 is contemplated. The cap orifice 38 is configured so that it is coincident with the injector lumen 20 so that medication flowing out will generally travel through the film 32 and through the cap orifice 38 with minimal resistance.

Figure 3:
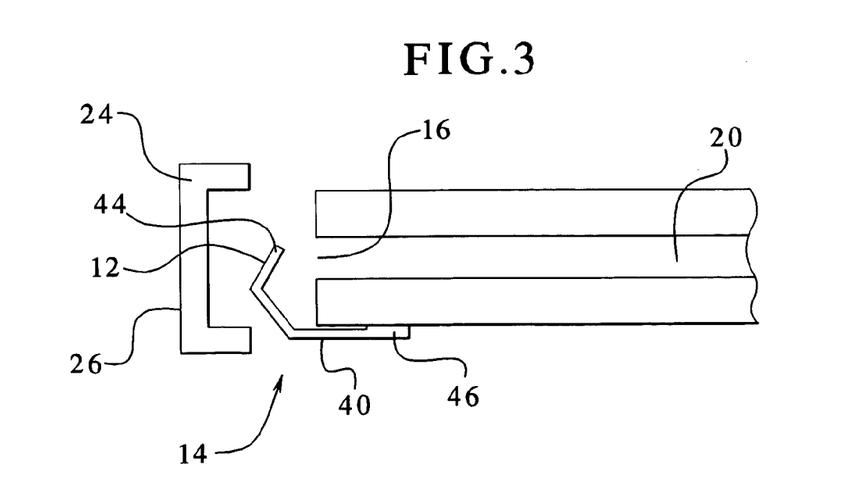
FIG. 3 is another embodiment of the invention showing one blocking mechanism.

FIG. 3 demonstrates one embodiment of the invention. Shown is an injection prevention component 40 generally, but not exclusively, located distal to the distal end orifice 16. In other embodiments, the injection prevention component may be proximal to part of the cap distal face 26. In one embodiment, the injection prevention component 40 may comprise an orifice shield 42, which generally covers or blocks (either partially or completely) the distal end orifice 16. One non-exclusive purpose of the orifice shield 42 is to interrupt the medication stream flow from the injector. It may do so by either blocking the entire stream path or part thereof. To facilitate the blocking or covering, the orifice shield 42 may be adapted to have a relatively flat face 44 or flat surface to maximize interruption or deflection. The injection prevention component may be attached to the injector assembly 10 via an injection prevention component attachment 46, which may include screws, adhesive, pins, slides, male-female receptacles, welds, bonds, bolts, or other well known mechanisms for attaching pieces together. The attachment and component may be anywhere along the injector.

The device 10 may also be fabricated as an integral piece or as separate pieces with the attachment 46. Thus, in the embodiment shown, since the cap 24 is not in place, the prevention component 40 extends out and blocks the path of the injector lumen 20. Thus, medication that sprays or is shot out, will generally impact the component 40 and prevent the accidental injection into the patient. Even if there is only partial blockage of the stream, then injection will likely not occur because the remaining stream may not have the required penetration velocity. Accordingly, the component 40 may be configured or adapted in such as way to be disposed distal to the distal end orifice 16, proximal to the cap proximal face 28, or proximal to part of the cap distal face 26.

Figure 4:
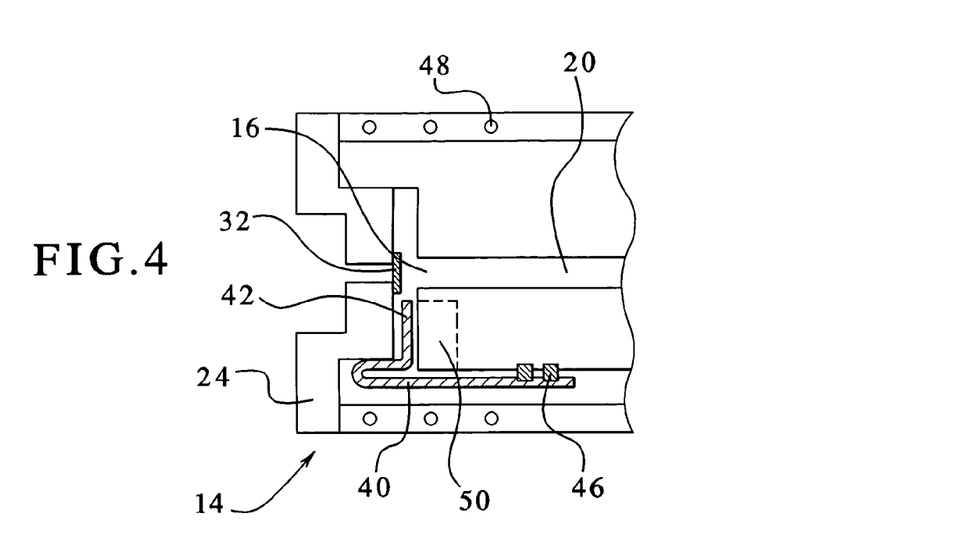
FIG. 4 is another embodiment of the invention showing one blocking mechanism.

FIG. 4 is another embodiment of the invention. Shown is the prevention component 40 moved out of the way by the cap 24. As the cap 24 moves into position, the cap pushes against the prevention component 40 so that it is no longer blocking the distal end orifice 16. Since the cap 24 is removable, the assembly 10 may also include a means 48 for biasing the cap. The mechanisms for biasing also are described in U.S. patent application Ser. No. 09/685,633, the disclosure of which is expressly incorporated by reference herein. The assembly 10 may also be configured to provide for an injection prevention component recess 50, in which the prevention component 40 may reside when the cap is put on. In this regard, the prevention component 40 may be neatly tucked in the recess 50. The prevention component 40 may also be adapted in such a way that it is totally out of the way of the distal end orifice 16 only when the cap 24 is firmly in place. Thus, as the cap proximal face 28 begins contacting the prevention component 40, the component 40 will begin to move out of the way of the distal end orifice 16. Thus, the component 40 can still block until the cap is completely on and in place. Once the cap is ejected off, the component 40 moves back into blocking position. Thus, the component may also include a leaf spring or other resilient/elastic material that can "spring" back into place when unrestrained.

Figure 5:
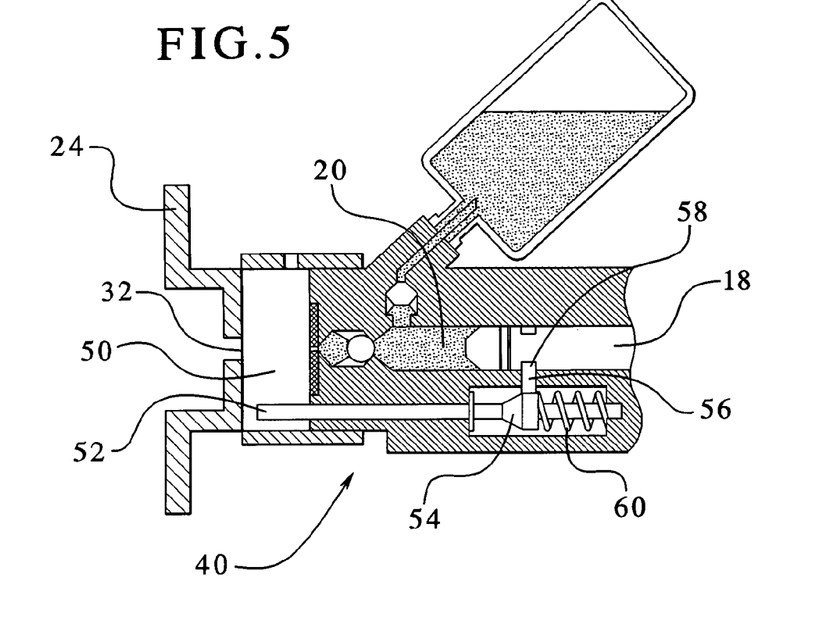
FIG. 5 is another embodiment of the invention showing one blocking mechanism.
Figure 6:
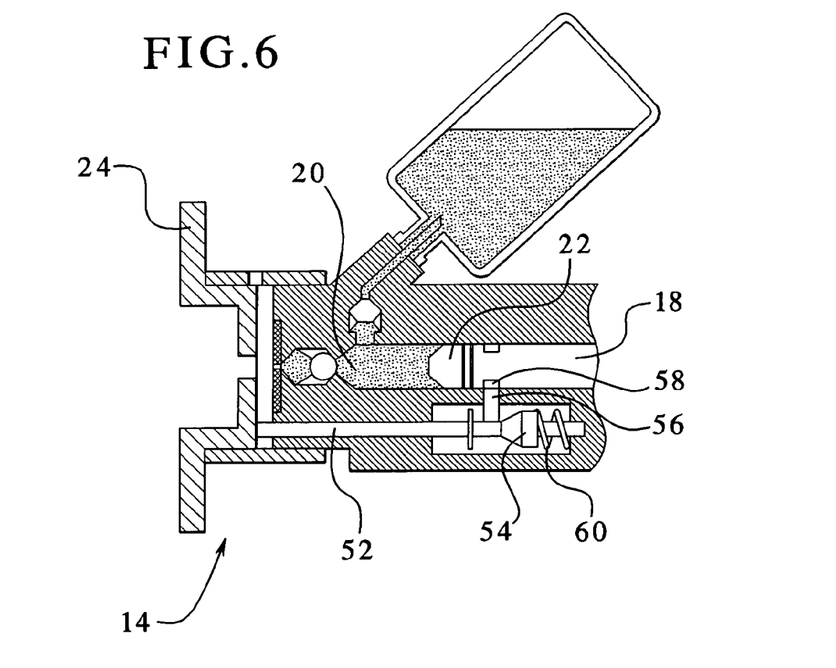
FIG. 6 is another aspect of the invention of FIG. 5.

FIGS. 5 and 6 demonstrate yet another embodiment of the invention. Shown is the injection prevention component 40 shown as a prevention piston 52, which is partially disposed within the recess 50. The prevention piston 52 includes a piston head 54 detachably attached to a lock pin 56. The lock pin 56 is adapted to move within an injector piston recess 58. When the lock pin 56 is in the recess 58, the injector piston 18 cannot move. Also included is a biasing means such as a prevention piston return means 60, which may include a spring, deformable material (such as rubber or plastic), screw, or the like. One purpose of the return means 60 is to move the prevention piston 52 back out and thus drop the lock pin 56, and accordingly, any means to bias the prevention piston 52 is contemplated, included those means for biasing the cap described in U.S. patent application Ser. No. 09/685,633.

It should be noted that any means for biasing can also include those means known in the art and can further include, but is not limited to, pistons, gears, rods, springs, worm gears, screws, deformable materials, electromagnets, optical components, and jacks. The means for biasing may also include various driving mechanisms, such as pneumatics, hydraulics, or manual drives. In addition, the means for biasing may also include phase change materials or other shape memory materials, such as those materials that change size or shape due to temperature application. One such material is Nitinol, which allows for size or shape transformation in its austenite and martensite states. Accordingly, the means for biasing is meant to include not only the structures described herein, but also, any acts or materials described herein, and also include any equivalent structures, equivalent acts, or equivalent materials; or structural equivalents, act equivalents, or material equivalents, to those described herein.

As shown in FIGS. 5 and 6, when the cap 24 approaches the distal end, it engages the prevention piston 52 and begins moving it inwards, thus compressing or deforming the return means 60. The lock pin 60, which was supported by the piston head 54, no longer has support and falls onto the piston 52 and thereby out of the injector piston recess 58.

Although not shown, the device 10 may be adapted to include a lock pin 56 that protrudes into the injector lumen 20 such that the lock pin 56 may engage the injector head 22, or be disposed distal to the injector head 22. Thus, the lock pin 56 need not solely enter the piston recess 58, but may interact with the piston 18 (or piston drive or release) in any fashion to keep it from moving forward, or otherwise interfere with the forward motion. Another embodiment of the invention may also include the orifice shield 42 as described above to be used in conjunction with the prevention piston assembly shown anywhere herein.

Figure 7:
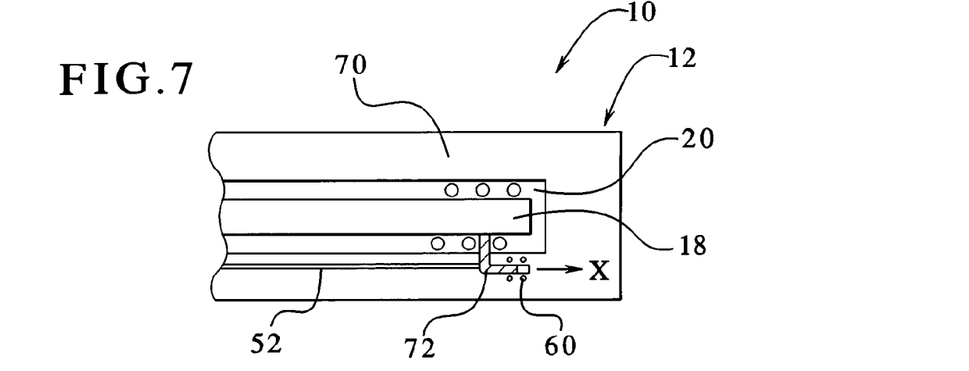
FIG. 7 is another embodiment of the invention showing one blocking mechanism.
Figure 8:
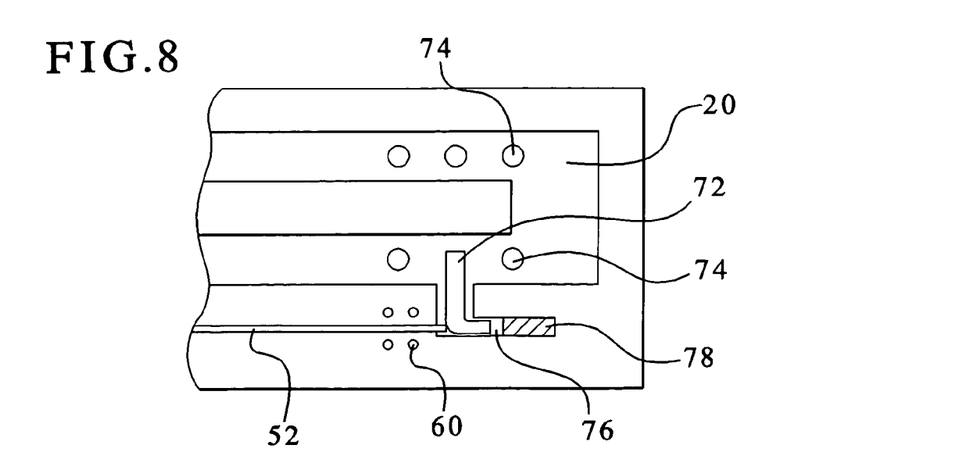
FIG. 8 is another embodiment showing the proximal end of the device.

FIG. 7 shows yet another embodiment of the invention. Shown is the injector assembly proximal end 12. In this embodiment, shown is the injector piston 18 and the injector piston biasing means 70. As described throughout, the means for biasing can also include those means known in the art and can further include, but is not limited to, pistons, gears, rods, springs, worm gears, screws, deformable materials, electromagnets, optical components, and jacks. The means for biasing may also include various driving mechanisms, such as pneumatics, hydraulics, or manual drives. In addition, the means for biasing may also include phase change materials or other shape memory materials, such as those materials that change size or shape due to temperature application. One such material is Nitinol, which allows for size or shape transformation in its austenite and martensite states. Accordingly, the means for biasing is meant to include not only the structures described herein, but also, any acts or materials described herein, and also include any equivalent structures, equivalent acts, or equivalent materials; or structural equivalents, act equivalents, or material equivalents, to those described herein.

In operation, as the prevention piston 52 is pushed in the direction from distal to proximal (the direction arrow X), then the piston 52 impacts against an injection prevention component 40, such as a latch 72. Latch 72 is adapted to interfere with the means for biasing the injection piston 74, which as described herein may include any biasing means above. In this regard, as the latch 72 engages or interferes with the means 74, it prevents the means from biasing the injection piston 18. As the cap 24 is placed on, it pushes the prevention piston 52 along, which impacts against the latch 72 and pushes the latch 72 into a latch recess 76. Associated with the latch recess 76 and the latch 72 is a means 78 for biasing the latch 72 back up into the interference position. The means 78 may also include a small wad of rubber or a spring that pushes the latch 72 back into the injector lumen 20.

In addition, the injection prevention component 40 may also be adapted to work in conjunction with orifice shields and/or prevention pistons as described herein. Moreover, the prevention component 40 may be adapted to work in conjunction with pneumatically driven locking means, as described in the contemporaneously filed U.S. patent application, (serial number unknown to be inserted later), entitled Injector Assembly with Driving Means and Locking Means, naming the following inventors, Boris V. Smolyarov and Victor T. Rogatchev, filed on (herewith); the disclosure of which is expressly incorporated by reference herein. In that disclosure, a mechanism including rollers, retainers, annular grooves, and ball locks are disclosed.

Figure 9:
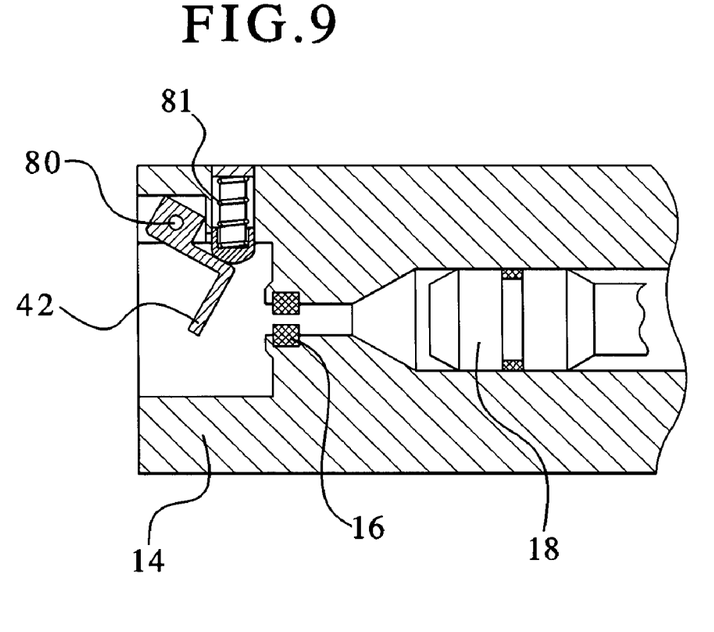
FIG. 9 is another embodiment showing an orifice shield.
Figure 10:
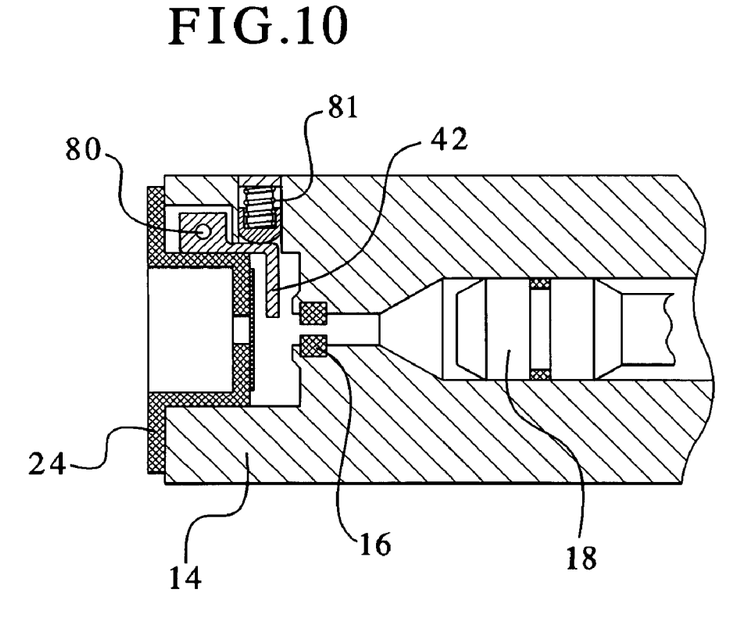
FIG. 10 is the embodiment of FIG. 9 in operation.

FIGS. 9 and 10, show another embodiment of the invention in which the orifice shield 42 interacts with a contained compression means 81, such as compression spring 81. The shield 42 pivots along an axle 80. In FIG. 9, when there is no cap pushing against the shield 42, the spring 81 is uncompressed and thereby pushes shield 42 in the way of the orifice. As the cap is put on, the shield 42 moves out of the way and compresses spring 81. As with any embodiment, the device may be adapted to hide the shield 42 away into a recess or otherwise out of the way.

In yet another embodiment of the invention, the invention may also comprise the various steps of operation. For example, also disclosed is a method of preventing the accidental injection of medication into a patient and reducing the risks of cross contamination during injections, comprising the steps of:

(a) loading a cap onto a distal end of an injector;

(b) disengaging a locking mechanism to permit a stream of medication to exit the injector;

(c) removing the cap after injection; and (d) engaging the locking mechanism to prevent a discharge of the medication.

Other steps parallel the steps described herein and the person of ordinary skill in the art would understand how to adapt the mechanism to further perform other steps. Thus, one embodiment of the invention may also include the process of adapting the device to include safety mechanisms as described herein.

It should be understood that the foregoing relates only to a limited number of embodiments that have been provided for illustration purposes only. It is intended that the scope of invention is defined by the appended claims and that modifications to the embodiments above may be made that do not depart from the scope of the claims.

We claim:

1. A multi-use, needle-free injector assembly having a proximal end and a distal end, the distal end having a distal end orifice, an injection piston located generally within an injector lumen, comprising:

(a) a removable cap generally distal to the distal end orifice, wherein the distal end orifice is distal to the injector lumen, the cap further including a cap distal face and cap proximal face;

(b) an injection prevention component disposed generally proximal to the cap distal face and distal to the distal end orifice;

(c) wherein the injection prevention component has a first injection prevention configuration to prevent the injector assembly from administering injectate to a subject at a sufficient pressure to pierce the skin and a second injection permitting configuration to permit the injector assembly to administer injectate to a subject, and (d) wherein the injection prevention component is reversibly movable between the first injection prevention configuration when the cap is removed and the second injection permitting configuration when the cap is in place.

2. The injector assembly of claim 1, wherein the cap further includes a cap orifice extending therethrough, the cap orifice also being coincident with the injector lumen.

3. The injector assembly of claim 2, wherein the cap further includes a film disposed over the cap orifice.

4. The injector assembly of claim 3, wherein the film comprises at least one of a plastic, rubber, polymer, polyethylene, polytetrafloroethylene, polyurethane, polyolefin, polypropylene, and polysulfone material; or combination thereof.

5. The injector assembly of claim 2, wherein the latch is adapted to disengageably engage with a proximal end of the injection piston.

6. The injector assembly of claim 5, wherein a rod is disposed between the cap proximal face and the injector lumen proximal end.

7. The injector assembly of claim 5, wherein the cap protective film comprises at least one of a plastic, rubber, polymer, polyethylene, polytetrafloroethylene, polyurethane, polyolefin, polypropylene, and polysulfone material; or combination thereof.

8. The injector assembly of claim 2, wherein the injection prevention component further includes at least one of an orifice shield, a piston, and a latch.

9. The injector assembly of claim 8, wherein the cap further includes a film disposed over the cap orifice.

10. The injector assembly of claim 9, wherein the film comprises at least one of a plastic, rubber, polymer, polyethylene, polytetrafloroethylene, polyurethane, polyolefin, polypropylene, and polysulfone material; or combination thereof.

11. The injector assembly of claim 9, wherein the orifice shield is disposed generally distal to the distal end orifice.

12. The injector assembly of claim 9, wherein the orifice shield is disposed generally proximal to the cap proximal face.

13. The injector assembly of claim 9, wherein the orifice shield includes a generally flat surface adapted to partially or completely block an injection stream distal of the distal end orifice to prevent the injector assembly from administering injectate to a subject at a sufficient pressure to pierce the skin.

14. The injector assembly of claim 9, wherein the orifice shield includes a generally flat surface adapted to block an injection stream distal of the distal end orifice to prevent the injector assembly from administering injectate to a subject at a sufficient pressure to pierce the skin.

15. The injector assembly of claim 9, wherein the orifice shield comprises a leaf spring.

16. The injector assembly of claim 9, wherein the orifice shield is detachably attached to a first side of the injector assembly.

17. The injector assembly of claim 9, wherein the orifice shield is adapted to cover the distal end orifice when the cap proximal face partially contacts the orifice shield.

18. The injector assembly of 17, wherein the orifice shield comprises a leaf spring.

19. The injector assembly of claim 18, wherein the orifice shield includes a generally flat surface adapted to generally block an injection stream distal of the distal end orifice to prevent the injector assembly from administering injectate to a subject at a sufficient pressure to pierce the skin.

20. The injector assembly of claim 9, wherein the piston further includes a lock pin.

21. The injector assembly of claim 20, wherein the lock pin protrudes into the injector lumen.

22. The injector assembly of claim 20, wherein the lock pin is adapted to interfere with the injection piston.

23. The injector assembly of claim 20, wherein the injection piston further comprises an injection piston recess adapted to detachably attach with the lock pin.

24. The injector assembly of claim 20, wherein the piston further comprises a rod disposed between the cap proximal face and the lock pin.

25. The injector assembly of claim 24, wherein the prevention component further comprises an orifice shield disposed distal to the distal end orifice.

26. The injector assembly of claim 24, wherein the film comprises at least one of a plastic, rubber, polymer, polyethylene, polytetrafloroethylene, polyurethane, polyolefin, polypropylene, and polysulfone material; or combination thereof.

27. The injector assembly of claim 9, wherein the latch is disposed at a proximal end of the injector lumen.

28. A multi-use, needle-free injector assembly having a proximal end and a distal end, the distal end having a distal end orifice, an injection piston located generally within an injector lumen, comprising:
 (a) a removable cap generally distal to the distal end orifice, wherein the distal end orifice is distal to the injector lumen, the cap further including a cap distal face and a cap proximal face; and
 (b) a means for preventing the injection piston from moving from a locked position to a discharged position wherein said means are partially located distal to the distal end orifice and
 (c) wherein said means are in the locked position when the cap is removed and said means are in the discharged position when said cap is in place.

29. The injector assembly of claim 28, wherein the means for preventing the injection piston from moving includes at least one of an orifice shield, a piston lock, and a latch.

30. The injector assembly of claim 29, wherein a film is disposed over a cap orifice.

31. The injector assembly of claim 30, wherein the film comprises at least one of a plastic, rubber, polymer, polyethylene, polytetrafloroethylene, polyurethane, polyolefin, polypropylene, and polysulfone material; or combination thereof.

32. The injector assembly of claim 31, wherein the cap proximal face is disconnectedly connected to the means for preventing the injection piston from moving.

33. A method of preventing the accidental injection of medication into a patient and reducing the risks of cross contamination during injections, comprising the steps of:
 (a) loading a cap onto a distal end of an injector having a distal end orifice
  thereby disengaging a locking mechanism partially located distal to the distal end orifice to permit a stream of medication to exit the injector; and
 (b) removing the cap after injection
  thereby engaging the locking mechanism to prevent a discharge of the medication.

* * * * *